United States Patent [19]

Ross et al.

[11] Patent Number: 5,062,959

[45] Date of Patent: Nov. 5, 1991

[54] PROCESS FOR THE ENRICHMENT AND/OR ISOLATION OF HEART GLYCOSIDES WITH THE USE OF NON-POLAR ABSORBER RESINS

[75] Inventors: Carl H. Ross, Viernheim; Rudolf Machat, Mannheim; Werner Häring, Heppenheim/Kirschhausen; Gustav Lettenbauer, Lampertheim, all of Fed. Rep. of Germany

[73] Assignee: Boehringer Mannheim GmbH, Mannheim, Fed. Rep. of Germany

[21] Appl. No.: 581,147

[22] Filed: 581147

Related U.S. Application Data

[63] Continuation of Ser. No. 418,695, Oct. 2, 1989, abandoned, which is a continuation of Ser. No. 250,692, filed as PCT EP87/00775 on Dec. 12, 1987, published as WO88/04663 on Jun. 30, 1988, abandoned.

[30] Foreign Application Priority Data

Dec. 20, 1986 [DE] Fed. Rep. of Germany ....... 3642760

[51] Int. Cl.⁵ .............................................. B01D 15/08
[52] U.S. Cl. ................................... 210/635; 210/656; 514/26; 536/5; 536/6.3; 536/127; 536/128
[58] Field of Search .................. 536/4.1, 5, 6.3, 127, 536/128; 514/26; 210/635, 656, 198.2, 658, 198.3, 502.1

[56] References Cited

U.S. PATENT DOCUMENTS

| | | | |
|---|---|---|---|
| 2,557,916 | 9/1951 | Rosen | 536/6.3 |
| 4,138,474 | 2/1979 | Updike | 210/504 |
| 4,147,764 | 4/1979 | Levy | 502/7 |
| 4,151,254 | 4/1979 | Gimovsky | 210/282 |
| 4,166,104 | 8/1979 | Wagner | 436/500 |
| 4,301,139 | 11/1981 | Feingers | 210/264 |
| 4,434,236 | 2/1984 | Freytag | 210/656 |
| 4,654,311 | 3/1987 | Khanna | 210/656 |
| 4,764,601 | 8/1988 | Reuning | 210/198.2 |

FOREIGN PATENT DOCUMENTS

| | | | |
|---|---|---|---|
| 2554767 | 4/1985 | France | 210/656 |
| 57-165400 | 10/1982 | Japan | 536/6.3 |

OTHER PUBLICATIONS

Chemical Abstracts, vol. 101, p. 410, Sep. 1984, Abstract 97633y.
Snyder, Introduction to Modern Liquid Chromatography John Wiley & Sons, Inc., New York, 1979, pp. 487-494.

*Primary Examiner*—Ernest G. Therkorn
*Attorney, Agent, or Firm*—Felfe & Lynch

[57] ABSTRACT

Enrichment and purification of heart glycosides from mixtures of mother liquors is achieved by absorption on non-polar, large-pored resins from aqueous solution with possible addition of solvents miscible with water, and subsequent desorption with water/solvent mixtures or pure solvents.

3 Claims, 1 Drawing Sheet

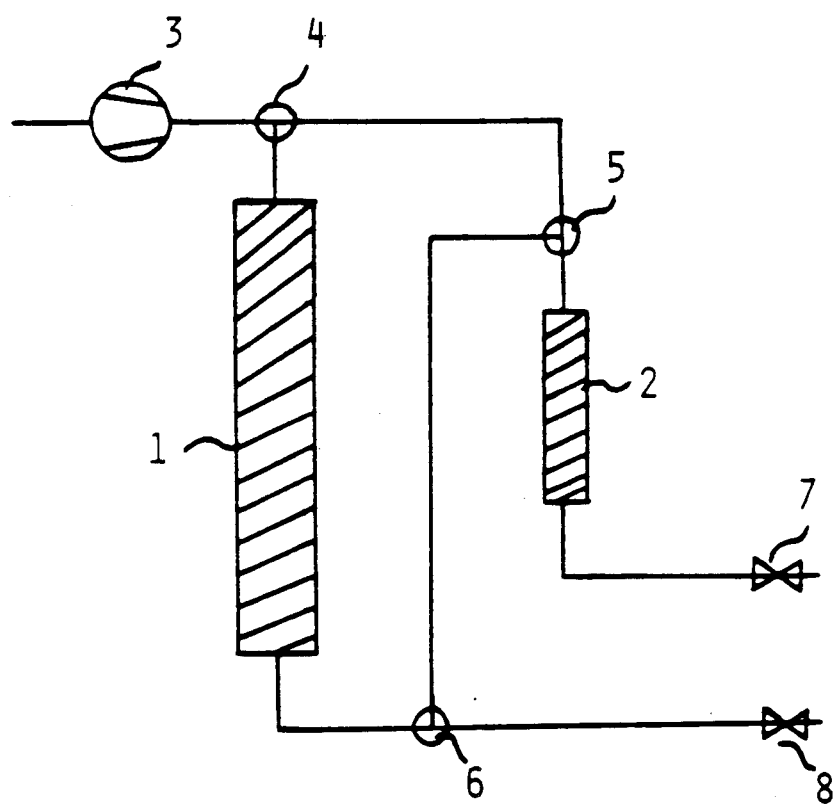

PROCESS FOR THE ENRICHMENT AND/OR ISOLATION OF HEART GLYCOSIDES WITH THE USE OF NON-POLAR ABSORBER RESINS

This is a continuation of application Ser. No. 418,695 filed on Oct. 2, 1989, which is a continuation of application Ser. No. 250,692 filed as PCT EP87/00775 on Dec. 12, 1987 published as WO88/04663 on Jun. 30, 1988, both now abandoned.

The subject of the present invention are processes for the working up of mixtures containing cardiac glycosides, such as crude extracts, products of chemical changes and crystallisation steps, as well as mother liquors.

By cardiac glycosides are understood compounds of the general formulae I, II or III

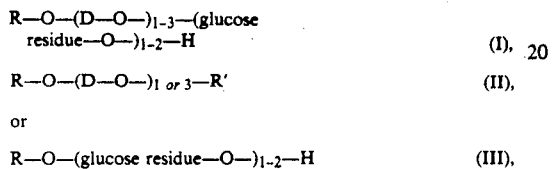

wherein, in each case, R signifies an aglycone, R' hydrogen, a methyl or acetyl group and D a desoxysugar residue (cf. Ullmann, 3rd ed., Volume 8, pp. 222–231).

For the isolation of cardiac glycosides, such as digoxin, metildigoxin, strophanthrins, lanatosides, from mixtures such as are obtained e.g. in the case of extraction of plant parts, chemical changes and crystallisation operations, laborious processes are generally needed, such as multiple counterflow partition, redissolvings and reprecipitations (cf. for example: Ullmann, loc. cit.).

These processes require the use of large amounts of potentially environment-endangering organic solvents, such as chloroform, dichloromethane, trichloroethylene. The handling of these solvents in large amounts leads to a large technical expense for maintaining the quality of air and water. Additionally the loss of valuable glycosides in non-utilisable mother liquors and concentrates is high.

The invention here is designed to alleviate these problems. The invention, as it is characterised in the claims, solves the task of making available processes for the enrichment and isolation of cardiac glycosides from mixtures, such as crude extracts, products of chemical changes and crystallisation steps, as well as from mother liquors, which manages as far as possible without the potentially environment-endangering solvents required according to the state of the art and, in addition, decreases the losses of valuable glycosides and thus increases product yields.

BRIEF DESCRIPTION OF THE DRAWING

The sole FIGURE shows apparatus suitable for Example 6's recovery of digoxin.

DESCRIPTION OF THE PREFERRED EMBODIMENTS

It has been found that the enrichment and purification of the cardiac glycosides from the mixtures 100 to 1000 m²/g and mother liquors described above in detail can be achieved by adsorption on non-polar, large-pored resins from aqueous solutions, possibly with the addition of solvents miscible with water, and subsequent desorption with water-solvent mixtures or pure solvents. It is especially surprising that a separation of the glycoside mixtures into individual compounds or groups is thereby simultaneously possible by variation of the composition of the desorption solution.

The isolation of valuable materials, such as antibiotically-active cephalosporins, from highly diluted solutions with the help of polymeric non-polar resins has been known for a long time. The problem of the enrichment and isolation of cardiac glycosides from complex cardiac glycoside mixtures and especially the dangerous conditions caused by the solvents necessary therefor has been known even longer. Thus, the present invention satisfies a long-existing need.

The adsorption and desorption necessary for the enrichment and isolation according to the invention can be carried out continuously or discontinuously (batch process). Preferably, however, this process is carried out on a column under slight pressure of 1 to 10 bar at temperatures of 20° to 50° C., preferably at room temperature.

For this purpose, one applies to a column filled with a suitable resin the aqueous solution of a crude extract or contaminated glycoside mixture, possibly with the addition of 1–80% of lower alcohols, preferably methanol, ethanol or isopropanol, or of lower ketones, preferably acetone, after the fat-like components have been removed by treatment of the crude extract with a non-polar solvent, preferably hexane, toluene, isohexane or petroleum ether.

All strongly polar materials, such as sugars, are removed from the loaded column by rinsing with water. By the addition of solvents miscible with water, preferably alcohols, lower ketones or cyclic ethers, by addition of salts and adjustment of a particular pH value, the elution solution is so varied that individual cardiac glycosides or groups of glycosides are desorbed from the resin. All solvents can be so chosen that they are as environmentally compatible as possible. The large amounts of chlorinated hydrocarbons necessary for the pre-purification can thereby be avoided.

As adsorbents, there are suitable non-polar adsorber resins with large surface area. Especially suitable large-pored, non-ionic resins, such as preferably cross-linked styrene polymers, acrylic ester polymers and/or styrene-divinylbenzene co-polymers. Also suitable are resins which can be chemically modified, especially halogenated or physically classified, such as sieved, made uniform in grain size and/or surface area. Preferably the resins will have a specific surface area of from 100 to 1000 m²/g.

Such resins are obtainable e.g. under the designations Amberlite XAD (trade mark: Rohm and Haas Co.), Diaion HP (trade mark: Mitsubishi Chemical Industries Limited) or Sepabeads SP (trade mark: Mitsubishi Chemical Industries Limited), in each case in series with different surface and adsorption properties. For example:

|  | chemical structure | specific surface area m²/g. resin |
|---|---|---|
| Amberlite ® XAD-2 | CAS-Reg.No.*) 9060-05-3 | |
| Amberlite ® XAD-4 | CAS-Reg.No.*) 37380-42-0 | 725 |
| Amberlite ® XAD-7 | CAS-Reg.No.*) 37380-43-1 | 450 |

-continued

| | chemical structure | specific surface area m²/g. resin |
|---|---|---|
| Diaion ® HP 10 | —CH₂CHCH₂CH— (with two phenyl rings) | 501 |
| Diaion ® HP 20 | | 718 |
| Diaion ® HP 30 | | 570 |
| Diaion ® HP 40 | | 705 |
| Diaion ® HP 50 | | 590 |
| Sepabeads ® SP 207 | —CH₂CH— (with phenyl ring) | 400 |

*) Chemical Abstracts Service Register Number

Within these series, there is also differentiated according to grain size.

| | chemical structure | specific surface area m²/g. resin |
|---|---|---|
| Diaion ® HP 20 SS | (such as Diaion ® HP 20) | |
| Diaion ® HP 2MG | $-CH_2C(CH_3)(COOCH_2)-CH_2C(CH_3)(COOR)-$ with $(CH_2)_n$ bridge and $-CH_2C(CH_3)(COOCH_2)-$ | 550 |
| Diaion ® HP 21 and Diaion ® HP 21 SS | (such as Diaion ® HP 20) | 700 |

The 4 last-mentioned resins have proved to be especially suitable. Especially, however, Diaion ® HP 20 SS and HP 21 SS.

The differing adsorption ability of the various resin types can be combined to especially expedient separation processes.

One desorbs further plant component materials, such as chlorophyll, by application of organic solvents, preferably alcohols, ketones or esters, to the column. After evaporation of the so obtained solutions, pure materials are obtained by redissolving and reprecipitation, possibly with the addition of adjuvants, preferably active charcoal, aluminium oxide or fullers' earth (such as floridin). Alternatively to the energy-expensive evaporation, the isolation can take place from aqueous solutions by adsorption on a polymeric resin and desorption with an organic solvent.

The invention is explained in more detail by the following Examples:

EXAMPLE 1

Digoxin

To a column filled with 410 ml. Diaion ® HP 20 SS (manufacturer: Mitsubishi, Japan) are applied 3.6 l. of aqueous/methanolic crude extract from Digitalis lanata after previous fermentation, saponification and defatting. The extract contains 117 g. of dry substance with a digoxin content of 1.95 g. After rinsing with 4.9 l. of water, 12.2 g. of dry substance with 1.95 g. digoxin are retained on the column.

After elution at 3 bar with aqueous isopropanol, one obtains fractions which are highly enriched in digoxin. 6.3 l. of 15% isopropanol solution are combined and concentrated to 100 ml. The crude digoxin fraction (4.9 g.) crystallising out is dissolved hot in 50 ml. methanol/chloroform 1:1, treated with active charcoal and filtered over 7.5 g. aluminium oxide. One washes with 80 ml. methanol/chloroform 1:1, concentrates the collected filtrates to 50 ml. and precipitates with 65 ml. diisopropyl ether. One isolates 1.4 g. digoxin (obviously a preparative amount).

EXAMPLE 2

Lanatoside C 20 g. of dry extract of the genuine glycosides from Digitalis lanata (content: lanatoside C 12%, about 1% digoxin, about 1.5% α-acetyldigoxin) are dissolved in 150 ml. water and 45 ml. methanol. This solution is applied with 1.4 l./h. flow rate to a column with 410 ml. Diaion ® HP 20 SS. One subsequently elutes with a pressure of 4–5 bar with water to which are added increasing amounts of methanol. From 50% methanol content, the glycosides can be detected in the eluate in the sequence lanatoside C, digoxin, α-acetyldigoxin, β-acetyldigoxin, lanatoside A. The fraction of 6 l. with 55% methanol is completely evaporated (2.53 g. with 60–70% lanatoside C and 3% digoxin) and recrystallised from ethanol with the addition of active charcoal. One obtains 1.0 g. of pure lanatoside C (obviously a preparative amount). The mother liquor residue and mixed fractions are again purified and separated over the column.

EXAMPLE 3

K-Strophanthin 20 g. of dry substance of Strophanthus kombé seeds defatted with hexane are dissolved in 100 ml. of water and pumped on to a column filled with 410 ml. Diaion ® HP 20 SS.

All non-glycosides are washed out with 4.2 l. of water at 4–5 bar and a flow rate of 1.4 l./h. (8.3 g. dry substance).

After addition of 45% methanol to the elution liquid, one obtains 7.8 l. of liquid with the glycosides. It is evaporated (6.9 g.), dissolved in ethanol, treated with active charcoal and precipitated with diisopropyl ether. There are obtained 6.06 g. of pure glycoside mixture (75% γ-K-strophanthin, 12.5% β₁-K-strophanthin, 9.5% β₂-K-strophanthin). Without great further working up, the mixture already corresponds to the requirements of the pharmacopoeias.

EXAMPLE 4

γ-K-strophanthin and β₂-K-strophanthin 20 g. of dry substance as from Example 3 are applied to 410 ml. Diaion ® HP 20 SS. One elutes the column with water with a methanol content increasing to 30%. The so obtained fractions (dry substance: 10.1 g.) contain no glycosides of K-strophanthin. The fraction (2.8 l.) with 40% methanol gives, after evaporation, 5.3 g. γ-K-strophanthin. After increasing the proportion of methanol to 45%, there is obtained a mixed fraction (7.5 l.) (3.0 g. of evaporation) of γ-, β₁- and β₂-K-strophanthin, 2.1 l. of eluate with 50 percent methanol contain 0.61 g. (dry substance) β₂-K-strophanthin.

EXAMPLE 5 g-Strophanthin

Mother liquor from ethanol extracts of Strophanthus gratus seeds, which is no longer to be brought to crystallisation but still contains glycoside, is brought to dryness.

20 g. of dry substance are dissolved in 100 ml. 10 percent methanol and pumped with 0.9 l./h. flow rate to a column with 410 ml. Diaion ® HP 20 SS. With 4 l. 10 percent methanol, one elutes all sugar components and polar non-cardiac glycosides.

After increasing the methanol content to 20%, one rinses g-strophanthin (3.69 g.) from the column with 3 l. at 3-4 bar and a flow rate of 1.4 l./h. After evaporation, it is recrystallised from water with addition of active charcoal. One obtains 2.12 g. of pure g-strophanthin (obviously a preparative amount).

EXAMPLE 6

Digoxin (cf. drawing)

60 g. dry extract (contains about 1.0 g. digoxin)—prepared by aqueous/methanol extraction of Digitalis lanata, fermentation, saponification, defatting and drying—are dissolved in 120 ml. methanol and 480 ml. water, adjusted with concentrated ammonia solution to pH 7.5 and pumped by means of the pump (3) to the column (1) filled with 410 ml. Diaion ® HP 2MG. Valve (6) is set to flow-off (8). After rinsing with 2.2 l. of water and 3.8 l. methanol/water (v/v 25:75), there are obtained in the flow-off, after evaporation, 54.8 g. of dry substance which contain no cardiac glycosides. The valves (6) and (5) are now so set that the flow-off from column (1) leads to column (2) filled with 50 ml. Diaion ® HP 20 SS. 5 l. of elution solution methanol/water (v/v 45:55) contain no digoxin in the flow-off (7). Fractions with subsidiary glycosides can be worked up separately. Valves (4) and (5) are now so set that the elution solution is applied directly to column (2). After 1 l. of a methanol/water mixture (v/v 50:50) which contains 0.9 g. of dry substance with 27% digoxin are returned to the separation process, it is eluted with 1.5 l. of a methanol/water mixture (v/v 55:45). This fraction is evaporated, redissolved from methanol/water, dissolved in methanol/chloroform, treated with active charcoal and aluminium oxide and precipitated with diisopropyl ether. One isolates 684 mg. of digoxin of high purity.

The process of Example 6 is further explained on the basis of the drawing. It shows merely one possible embodiment of the flow diagram.

The references mean therein
(1) column filled with 410 ml. Diaion ® HP 2MG
(2) column filled with 50 ml. Diaion ® HP 20 SS
(3) pump
(4) 3-way valve
(5) 3-way valve
(6) 3-way valve
(7) flow-off valve
(8) flow-off valve.

EXAMPLE 7

Metildigoxin 10 g. of the mixture of mainly $\beta$-metildigoxin (60-65%), $\alpha$-metildigoxin (about 7.5%), digoxin (15-20%) and dimethyl ethers of digoxin (about 8%), obtained from the methylation of digoxin with dimethyl sulphate, are dissolved warm in 85 ml. ethanol abs. and 12 ml. water and filtered clear. This solution is pumped on to a column with 410 ml. HP 20 SS which had previously been rinsed with ethanol 30%. Subsequently, it is rinsed with water with increasing ethanol content under a pressure of 4 bar and a flowthrough of about 1 l./hour.

4.75 l. of eluate with 40% ethanol contain 3.91 g. of solid material. The mixture contains all non-reacted digoxin, $\alpha$-metildigoxin and $\beta$-metildigoxin and can again be separated on the column. The following fraction of 5 l. contains 4.73 g. of slightly contaminated $\beta$-metildigoxin. If the ethanol content is increased, diethers and higher ethers of digoxin are eluted. The main fraction with metildigoxin is reprecipitated from methanol/water, boiled up with chloroform and stirred up with acetone.

One obtains 3.65 g. $\beta$-metildigoxin of standard quality.

EXAMPLE 8

Digoxin 120 g. of dry extract with a digoxin content of about 1.9 g. (cf. Example 6) are dissolved at room temperature in 960 ml. water, 240 ml. ethanol and 5 ml. concentrated ammonia solution and filtered clear. The solution is pumped to a column with 410 ml. Diaion ® HP 20. (Pressure 2 bar, flow rate 1-1.2 l./hour).

Column run-off and 1.8 l. of rinsing water contain 87.2 g. of dry substance free from cardiac glycosides.

There follow elutions with 4.4 l. ethanol 20% and 2.4 l. ethanol 27.5%. The latter contains small amounts of digoxin (<2.5%) and is used again.

5.0 l. of eluate ethanol 40% contain the main amount of digoxin (8.3 g. dry substance, about 20% digoxin). After an intermediate fraction (1.2 l.) of ethanol 43%, which is returned, the column is rinsed with pure ethanol for the next cycle. In the first 2 l. of the rinsing ethanol, one finds the main amount of the digitoxin (dry residue 3.5 g., 10% digitoxin) which can be obtained therefrom. The digoxin fraction is concentrated by distillation to 1.42 l. and pumped to a column with 410 ml. HP 20 SS (pressure 4-10 bar, flow rate 1.2 l./hour). The column run-off of 1.5 l. and the fractions with ethanol 20% (1.5 l.), ethanol 24.5% (4.6 l.) and ethanol 27% (3.75 l.) contain no digoxin. After a rinsing with ethanol 33% (0.5 l.) for the separation of digoxigenin-bis-digitoxoside, the ethanol content is increased to 40%.

One collects 6 fractions of 0.39 l. The fractions 1, 5 and 6 are used for the elution of the HP 20 column. 1.86 g. of digoxin are contained in 3.72 g. of dry substance of eluates 2, 3 and 4. For regeneration, the column is rinsed with pure ethanol. The crude digoxin is dissolved warm in 50 ml. ethanol/water 1:1, concentrated to 25 ml., cooled and filtered off with suction. One obtains 1.85 g., which are dissolved in chloroform/methanol 9:1, treated with silica gel and active charcoal and concentrated. The crystallisate is boiled up in ethanol with the addition of ammonia, filtered off hot with suction and dried. There are obtained 1.1 g. of pure digoxin.

EXAMPLE 9

Digoxin, Gitoxin, Digitoxin

One dissolves 50 g. of defatted dry extract of Digitalis lanata (as in Example 6) in 415 ml. of water, 154 ml. methanol and 2 ml. concentrated ammonia solution. The clear filtered solution is pumped on to a column with 470 ml. Diaion ® HP 21 SS. It is subsequently fractionally eluted with a pressure of 4 bar and a flow rate of 1.0 l./hour.

Column runoff up to 55% methanol (1.59 l.) contain 43.4 g. of dry substance of non-identified sugars and glycosides.

The last fractions contain digoxigenin-bis-digitoxoside highly enriched and can be worked up to this glycoside.

2.5 l. of eluate with 65% methanol proportion contain 1.12 g. of dry substance with over 60% digoxin which, after usual purification steps, gives 0.52 g. of pure digoxin. In the fractions with 70% methanol (2.5 l.) are small amounts of digoxin. These are again applied to the column.

1.5 l. of fraction (80% methanol) contain, highly enriched, the glycoside gitoxin and can be worked up to this. 0.81 g. of the fraction with pure methanol (0.9 l.) contain 80 mg. of digitoxin which can be isolated from this fraction.

We claim:

1. A process for the enrichment of and/or isolation of cardiac glycosides from a crude extract in which an aqueous solution of the extract is subjected to adsorption and desorption on non-polar, non-ionic resin based on crossed-linked styrene polymers, acrylic ester polymers and/or styrene-divinyl benzene copolymers, said resin having a specific surface area of from 100 to 1000 $m^2/g$ and in which an eluant consisting of a mixture of water and an organic solvent which does not contain chlorinated hydrocarbons is used in the desorption step to obtain a preparative amount of cardiac glycosides.

2. Process according to claim 1 in which, as eluant, there is used a mixture of water and lower alcohols or ketones in the ratio of from 99:1 to 20:80.

3. A process according to claim 1 in which the cardiac glycosides are digoxin, metildigoxin, strophanthins, lanatosides and mixtures thereof.

* * * * *